(12) United States Patent
Kanazawa et al.

(10) Patent No.: US 7,189,974 B2
(45) Date of Patent: Mar. 13, 2007

(54) EUV LIGHT SPECTRUM MEASURING APPARATUS AND CALCULATING METHOD OF EUV LIGHT INTENSITY

(75) Inventors: Hajime Kanazawa, Tochigi-ken (JP);
Akira Miyake, Tochigi-ken (JP);
Fumitaro Masaki, Tochigi-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 213 days.

(21) Appl. No.: 11/062,026

(22) Filed: Feb. 18, 2005

(65) Prior Publication Data
US 2005/0184248 A1    Aug. 25, 2005

(30) Foreign Application Priority Data
Feb. 20, 2004   (JP)   ............... 2004-044724

(51) Int. Cl.
*G01J 1/42* (2006.01)
(52) U.S. Cl. .................................... 250/373

(58) Field of Classification Search ........... 250/370.09, 250/372, 365; 378/36, 43, 82, 83, 84, 85
See application file for complete search history.

(56) References Cited

U.S. PATENT DOCUMENTS

| | | | | |
|---|---|---|---|---|
| 4,979,203 | A * | 12/1990 | Suckewer et al. | .......... 378/206 |
| 6,324,256 | B1 | 11/2001 | McGregor et al. | |
| 7,003,075 | B2 * | 2/2006 | Miyake et al. | ................ 378/82 |
| 2004/0129900 | A1 * | 7/2004 | Den Boef et al. | ....... 250/559.3 |

FOREIGN PATENT DOCUMENTS

| | | |
|---|---|---|
| JP | 10-73698 A | 3/1998 |
| JP | 2002-174700 A | 6/2002 |

* cited by examiner

*Primary Examiner*—David Porta
*Assistant Examiner*—David S. Baker
(74) *Attorney, Agent, or Firm*—Morgan & Finnegan LLP

(57) ABSTRACT

A measuring apparatus for measuring a spectrum of extreme ultraviolet light that diverges from a divergent center point of an extreme ultraviolet light source, includes a spectrum measuring unit that includes a spectrometer and a detector that has a spatial resolution in a spectrum forming direction of the spectrometer, and a drive mechanism that makes the spectrum measuring unit movable relative to the divergent center point.

6 Claims, 5 Drawing Sheets

EUV LIGHT SPECTRUM MEASURING APPARATUS AND CALCULATING METHOD OF EUV LIGHT INTENSITY

BACKGROUND OF THE INVENTION

The present invention relates to an extreme ultraviolet ("EUV") light spectrum measuring apparatus and an EUV light intensity calculating method used to evaluate an EUV light source (having a wavelength between 10 and 15 nm) for use with a projection exposure apparatus in a photolithography in manufacturing semiconductor devices.

Reduction projection exposures using ultraviolet have been conventionally employed to manufacture such fine semiconductor devices as a semiconductor memory and a logic circuit in the photolithography method. The critical dimension to be transferred by the reduction projection exposure is proportionate to a wavelength of light used for transfer, and inversely proportionate to the numerical aperture ("NA") of a projection optical system. In order to transfer a finer circuit pattern, a shorter wavelength of used ultraviolet ("UV") light has been promoted from an ultrahigh pressure mercury lamp i-line with a wavelength of about 365 nm to a KrF excimer laser with a wavelength of about 248 nm and an ArF excimer laser with a wavelength of about 193 nm.

However, the lithography using the UV light has the limits to satisfy the rapidly promoting fine processing to semiconductor devices, and a reduction projection exposure apparatus using the EUV light with a wavelength of about 10 to 15 nm much shorter than that of the ultraviolet has been developed to efficiently transfer a very fine circuit pattern of 0.1 μm or less.

A development of the EUV light source for the reduction projection exposure apparatus is promoted parallel to a development of the reduction projection exposure apparatus. One illustrative EUV light source is, for example, a laser excited EUV light source as disclosed in Japanese Patent Application, Publication No. 2002-174700 (corresponding to U.S. Pat. No. 6,324,256). The laser excited EUV light source irradiates a highly intensified pulse laser beam to a target material put in a vacuum chamber, and generates the high-temperature plasma. Among the lights having various wavelengths emitted from thus generated plasma, the EUV light utilizes the light having a wavelength, for example, of about 13 nm. The target material uses a metallic thin film, an inert gas, a droplet, etc., and is supplied to a vacuum chamber by such a means as a gas jet. The EUV light emitted from the plasma is generally condensed into a condensing point by a rotationally elliptic condenser mirror, is introduced into a projection exposure apparatus after diverging from the condensing point, and illuminates a mask uniformly via an illumination optical system of the projection exposure apparatus. Alternatively, the EUV light may be introduced, as light collimated by the rotationally elliptical condenser mirror, into the projection exposure apparatus.

In the exposure apparatus using the EUV light, an optical element in the optical system that introduces the EUV light mainly uses an oblique-incidence total reflection mirror and a Si/Mo multilayer coating mirror as a mirror having an incident angle close to normal incidence. Since the multilayer coating mirror for the normal incidence has a high reflectance to the EUV light having a wavelength around 13.5 nm, the EUV light for projection exposure generally uses a wave range between 13.365 nm and 13.635 nm around the wavelength of 13.5 nm among the lights emitted from the EUV light source. The throughput of the projection exposure apparatus depends upon the absolute value of the EUV light intensity in the wave range between 13.365 nm and 13.635 nm, and an exposure apparatus has a higher productivity as the absolute value increases.

The EUV light source needs to emit the EUV light at a high intensity in the wave range between 13.365 nm and 13.635 nm among the lights having various wavelengths. The light intensity in the non-exposure wave range should be low, because this light turns to the heat after absorbed in the optical element in the optical system, and deteriorates the of the optical system.

For these reasons, it is important to previously recognize a spectrum of the light emitted from the EUV light source for the exposure apparatus.

One illustrative, conventional EUV light spectrum measuring apparatus is disclosed, for example, in Japanese Patent Application, Publication No. 10-073698. According to this reference, a diffraction grating forms a spectrum of part of the EUV light (or referred to as "soft-X-ray" in this reference) emitted from the plasma as a light emitting point, making the light intensity of each wavelength measurable.

However, the above prior art can measure the spectrum of the light only in a specific divergent direction and cannot structurally measure the spectra in all the divergent directions. When the spectra differ according to divergent directions, the prior art cannot measure the spatial spectrum distribution or the intensity in the predetermined wave range, such as between 13.365 nm and 13.635 nm, in the entire divergent directions. In addition, the prior art disadvantageously cannot measure a total intensity in the predetermined wave range emitted from the light source.

BRIEF SUMMARY OF THE INVENTION

According to one aspect of the present invention, a measuring apparatus for measuring a spectrum of extreme ultraviolet light that diverges from a divergent center point of an extreme ultraviolet light source, includes a spectrum measuring unit that includes a spectrometer and a detector that has a spatial resolution in a spectrum forming direction of the spectrometer, and a drive mechanism that makes the spectrum measuring unit movable relative to the divergent center point.

Other objects and further features of the present invention will become readily apparent from the following description of the preferred embodiments with reference to accompanying drawings.

DETAILED DESCRIPTION OF THE PREFERRED EMBODIMENTS

A description will now be given of an embodiment of the present invention.

First Embodiment

Figure 1:
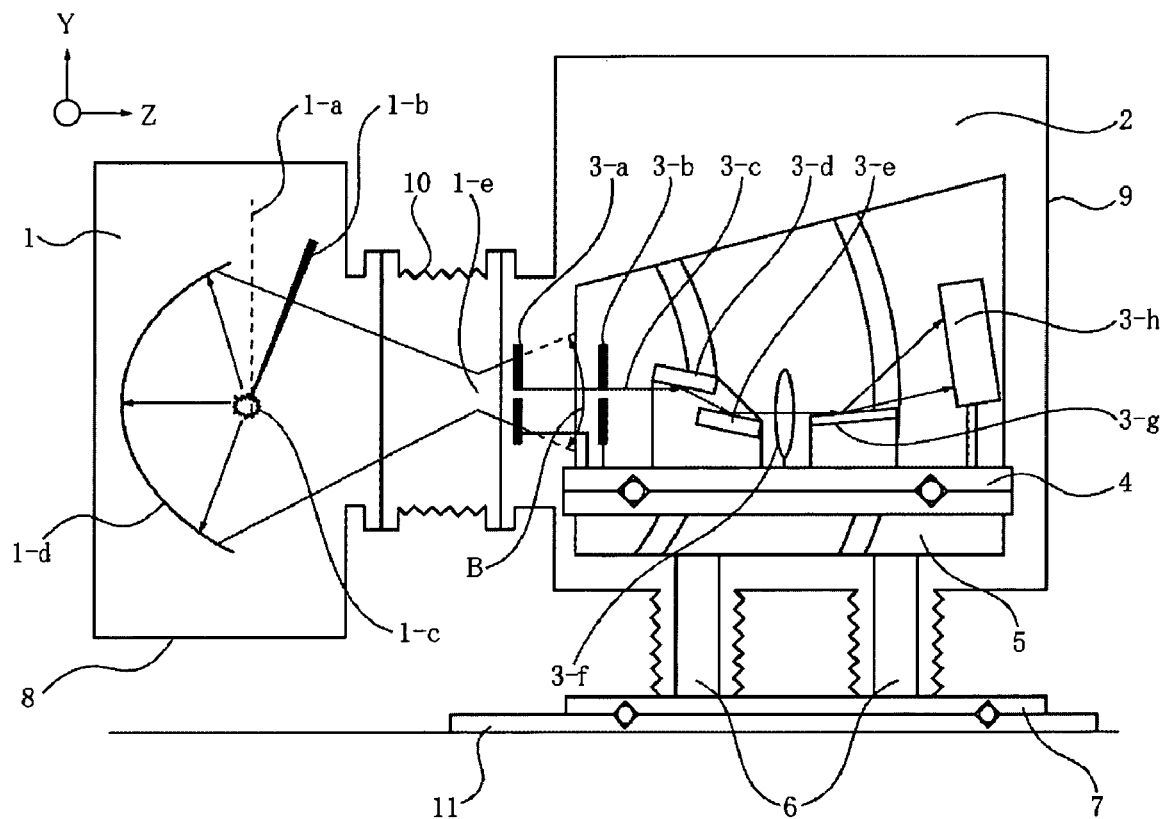
FIG. 1 is a sectional view of an EUV light spectrum measuring apparatus according to a first embodiment, and an EUV light source that generates the EUV light as an object to be measured.

FIG. 1 is a sectional view of an EUV light spectrum measuring apparatus according to a first embodiment, and an EUV light source that generates the EUV light as an object to be measured. The following description uses a coordinate that defines an X-axis as a direction perpendicular to the paper surface, a Y-axis as a longitudinal direction on the paper surface, and a Z-axis as a lateral direction on the paper in FIG. 1.

The light source as an object to be measured is the laser excited EUV light source in this embodiment. The laser excited EUV light source uses the plasma as a light emitting point generated mainly by irradiating a laser beam onto a target material, condenses the EUV light emitted from the light emitting point into a condensing point using a condenser mirror having a rotationally elliptic reflective surface, and then supplies the EUV light to the projection exposure apparatus.

The EUV light spectrum measuring apparatus of this embodiment measures a (spatial) distribution relating to a divergent angle of the spectrum distribution of the light emitted from the condensing point as the divergent center of the EUV light.

Instead of the EUV light that diverges from the condensing point by the condenser mirror, the light emitting point as the plasma is set to a divergent point of the EUV light in order to measure the spectrum distribution of the emitted light.

The object to be measured of present invention is applicable to another EUV light source rather than the laser excited EUV light source, such as, a gas discharge EUV light source. In this case, a structure of the apparatus is properly changed in accordance with the mechanical structure and the EUV light so as to obtain similar effects.

The EUV light source 1 radiates the pulsed EUV light by irradiating pulsed laser light 1-b to a target material 1-a supplied from a nozzle, and generates a plasma of the target material at a light emitting point 1-c. This EUV light is condensed into a condensing point 1-e as one focus by a rotationally elliptic condenser mirror 1-d having the light emitting point 1-c at the other focus. The EUV light diverges within the solid angle B from the light condensing point 1-e as the divergent center position. The condensing point 1-e is the light emitting point 1-c having a certain size, which is imaged by the condenser mirror 1-d as an enlargement optical system, and therefore the condensing point 1-e has a finite size greater than the light emitting point 1-c.

The inventive EUV light spectrum measuring apparatus 2 introduces the EUV light into a plane imaging diffraction grating 3-g via a light source position restricting aperture 3-a, an angle restricting aperture 3-b, high order light cutting mirrors 3-d and 3-e, a visible light cutting filter 3-f, etc., forms the spectrum, introduces the spectrum into the photodiode array 3-h as a photodetector and measures the spectrum of the light emitted from the EUV light source 1.

The light source position restricting aperture 3-a is provided near the condensing point 1-e so that only the EUV light is incident upon the measuring apparatus from a specific position on the condensing point 1-e.

The angle restricting aperture 3-b is arranged apart from the light source position restricting aperture 3-a by a predetermined distance, allows only the EUV light that has a specific directivity among the EUV lights that diverge after passing the light source position restricting aperture 3-a, and forms the EUV light 3-c that is a shaped narrow beam with an approximately single directivity.

It is preferable to introduce the EUV light 3-c to two high order light cutting mirrors 3-d and 3-e. The high order light cutting mirrors 3-d and 3-e are, for example, an oblique incidence type mirrors having a carbon coating, and used to cut the high order light that is closer to the short wavelength side than the wave range to be measured. The high order light is unnecessary order diffracted light which would be otherwise generated in the plane imaging diffraction grating 3-g, which will be described later, unless cut by the mirrors 3-d and 3-e. For example, the first order diffracted light having a wavelength of 13.5 nm and a second order diffracted light having a wavelength of 6.75 nm half of that of the first order diffracted light are generated at the same angle. Therefore, even when the photodiode array 3-h attempts to receive only the first order diffracted light having a wavelength of 13.5 nm emitted from the plane imaging diffraction grating 3-g so as to detect its intensity, the second order diffracted light having a wavelength of 6.75 nm also enters the same position on the photodiode array 3-h, precluding the precise intensity detection. The high order light cutting mirrors 3-d and 3-e cut the unnecessary order light and prevent the unnecessary order lights from entering the plane imaging diffraction grating 3-g.

If necessary, the visible light cutting filter 3-f made, for example, of a Zr thin film cuts the unnecessary visible light and infrared light. The high order light cutting mirrors 3-d and 3-e and the visible light cutting filter 3-f separate the light that is greatly apart from the exposure wavelength from the measured light having a spectrum to be measured, and prevents the light having unnecessary wavelengths from lowering the precision of the spectrum measurement in the target wave range. Without the above elements, the spectrum measurement precision lowers because the light having the unnecessary wavelengths, which is not an object of the spectrum measurement, heats optical elements, and causes the reflection to the photodiode array 3-h.

The plane imaging diffraction grating 3-g as a spectrometer disperses the wavelength of the EUV light 3-c wavelength in an approximately Y-axis direction, and introduces the EUV light into the photodiode array 3-h as a detector. In FIG. 1, the short wavelength is dispersed at a lower side on the paper, whereas the long wavelength is dispersed on an upper side. The photodiode array 3-h outputs a signal for each incident position or a signal corresponding to each wavelength, and thus the spectrum distribution can be measured. The photodiode array 3-h may use another detecting principle as long as it is a sensor having one-dimensional or two-dimensional resolution in a dispersion direction relative to the incident light intensity.

A spectrum or an intensity ratio of the EUV light in a specific direction for each wavelength, which EUV light diverges from a specific position restricted by the light source position restricting aperture 3-a at the condensing point 1-e and is restricted by the angle restricting aperture 3-b, is calculated by dividing every wavelength of an output value of the photodiode array 3-h by a reflectance of the high order light cutting mirrors 3-d and 3-e, the transmittance of the visible light cutting filter 3-f, the diffraction efficiency of the plane imaging diffraction grating 3-g, and a sensitivity for each position of the photodiode array 3-h.

The above spectrum measurement provides the spectrum distribution of the light emitted in a direction that connects the light source position restricting aperture 3-*a* to the angle restricting aperture 3-*b*, among the lights emitted from the EUV light source 1.

The angle dependency of the spectrum distribution can be obtained by rotating the EUV light spectrum measuring apparatus 2 that finishes the above measurements, around the condensing point 1-*e* and repeating similar measurements in respective directions.

The spectrum measuring means that includes the light source position restricting aperture 3-*a*, angle restricting aperture 3-*b*, high order light cutting mirrors 3-*d* and 3-*e*, visible light cutting filter 3-*f*, plane imaging diffraction grating 3-*g*, photodiode array 3-*h*, etc. This embodiment fixes the spectrum measuring apparatus onto a ωY stage 4 that rotates around the Y-axis and the condensing point 1-*e*, and fixes the ωY stage 4 onto a ωX stage 5 that rotates around the X-axis and the condensing point 1-*e*. Thereby, the spectrum measuring means is made rotatable as a whole by the ωY stage 4 and ωX stage 5 in an arbitrary direction around the condensing point 1-*e*. The spectrum of the EUV light that diverges from the condensing point 1-*e* in the arbitrary direction can be measured, and the spectra of the EUV light source that has different spectra according to diverging directions.

Figure 2:
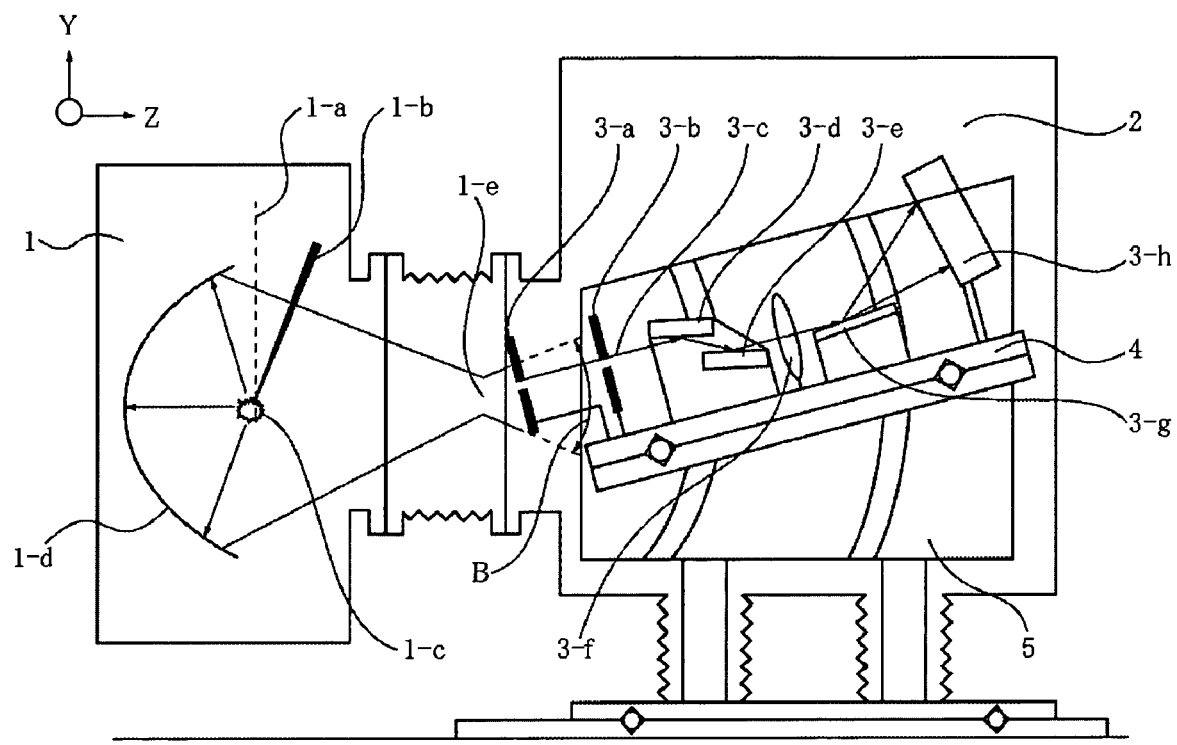
FIG. 2 is a view showing one embodiment of a rotation of the spectrum measuring means.

FIG. 2 is a view of an exemplary rotation of the spectrum measuring means. For example, as the ωX stage 5 is driven by a drive unit (not shown), the spectrum measuring means can be rotated around the X-axis around the condensing point 1-*e*, as shown in FIG. 2. Similarly, a rotation around the Y-axis is available by moving the ωY stage 4. A combination of these actions can measure the spatial spectrum distribution around the condensing point 1-*e*.

It is preferable to fix the ωX stage 5 onto a Y stage 6 that is movable along the Y-axis direction, and to fix the Y stage 6 onto an X stage 7 that is movable along the X-axis direction. This structure provides a translation of the spectrum measuring means as a whole on the plane perpendicular to the Z-axis as an optical axis of the EUV light source. The spectrum of the EUV light that diverges from the condensing point 1-*e* in the arbitrary direction can be measured, and the spectra of the EUV light source that has different spectra according to diverging directions.

Figure 3:
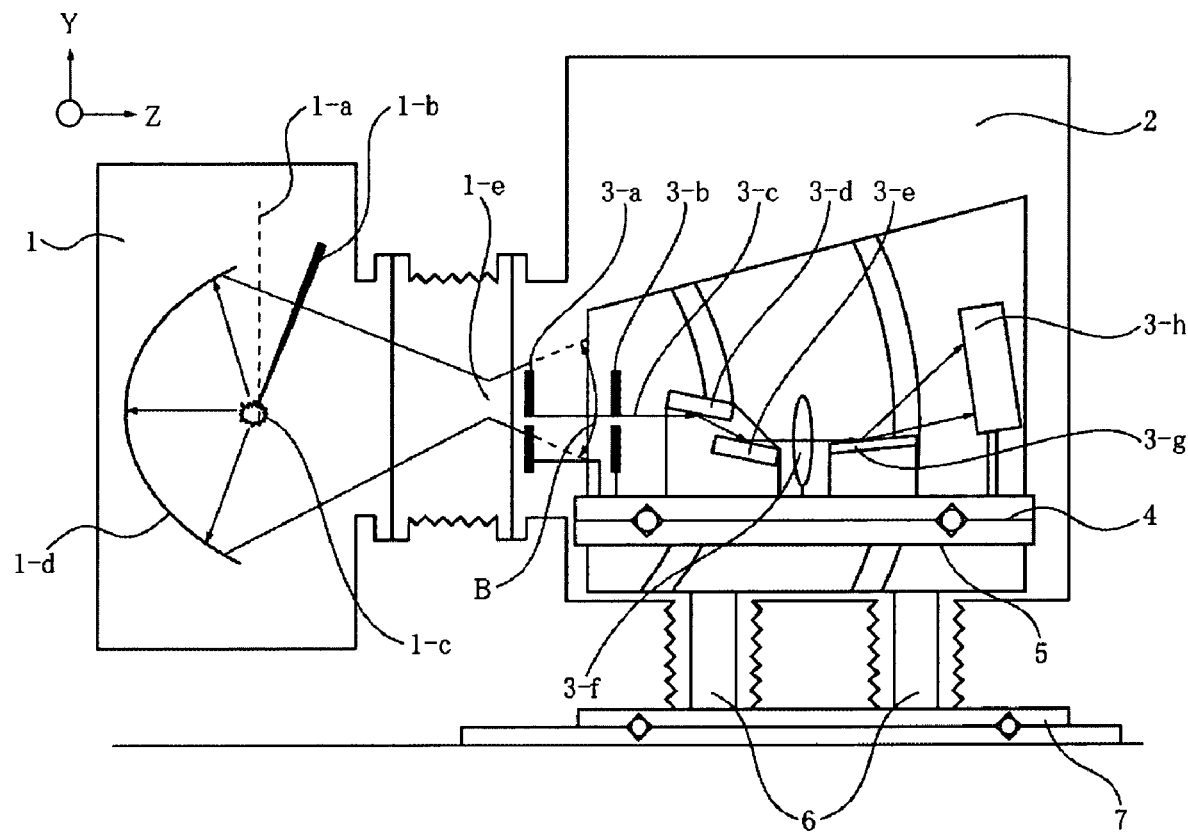
FIG. 3 is a view showing one embodiment of a translation of the spectrum measuring means.

FIG. 3 is a view showing an exemplary translation of the spectrum measuring means. For example, when the Y stage 6 is driven downwardly, the element in the spectrum measuring means translates in a minus direction along the Y-axis as shown in FIG. 3. While FIG. 1 measures the spectrum of the EUV light that diverges from the center point of the condensing point 1-*e*, FIG. 3 measures the spectrum of the EUV light that diverges from the lower portion of the condensing point 1-*e* on the paper surface.

This configuration provides the spectrum measurement of the EUV light emitted in an arbitrary direction from an arbitrary position on the divergent center point of the EUV light, and provides the angular dependency of the spectrum distribution.

The EUV light is absorbed in the air etc. The vacuum chambers 8 and 9 shown in FIG. 1 are provided to maintain the insides of the EUV light source 1 and the EUV light spectrum measuring apparatus 2 to be vacuum. The EUV light source 1 and the EUV light spectrum measuring apparatus 2 are connected by a vacuum bellows 10 that is maintained vacuum similar to the vacuum chambers 8 and 9. The EUV light from the EUV light source 1 reaches the EUV light spectrum measuring apparatus 2 through the hollow inside in the vacuum bellows 10. The vacuum bellows 10 allows translation driving by the Y stage 6 and the X stage 7. In order to maintain the vacuum chambers 8 and 9 to be vacuum, the air pressure applies the constriction force to the vacuum bellows 10. Since the EUV light source 1 and the base 11 in the EUV light spectrum measuring apparatus are fixed onto a fixing member (not shown), the EUV light's position along the optical axis does not change in the EUV light source 1 and the EUV light spectrum measuring apparatus 2, even when the air pressure changes occur so as to change the inside of the EUV light source 1 and the EUV light spectrum measuring apparatus 2 between the air pressure and the vacuum. It is preferable to prevent invasions of the stray light into the optical path of the EUV light by covering, with a stray light preventing tube that prevents an invasion of the scattered light into the optical path, the optical path of the EUV light to be measured in the EUV light spectrum measuring apparatus 2.

Second Embodiment

Figure 4:
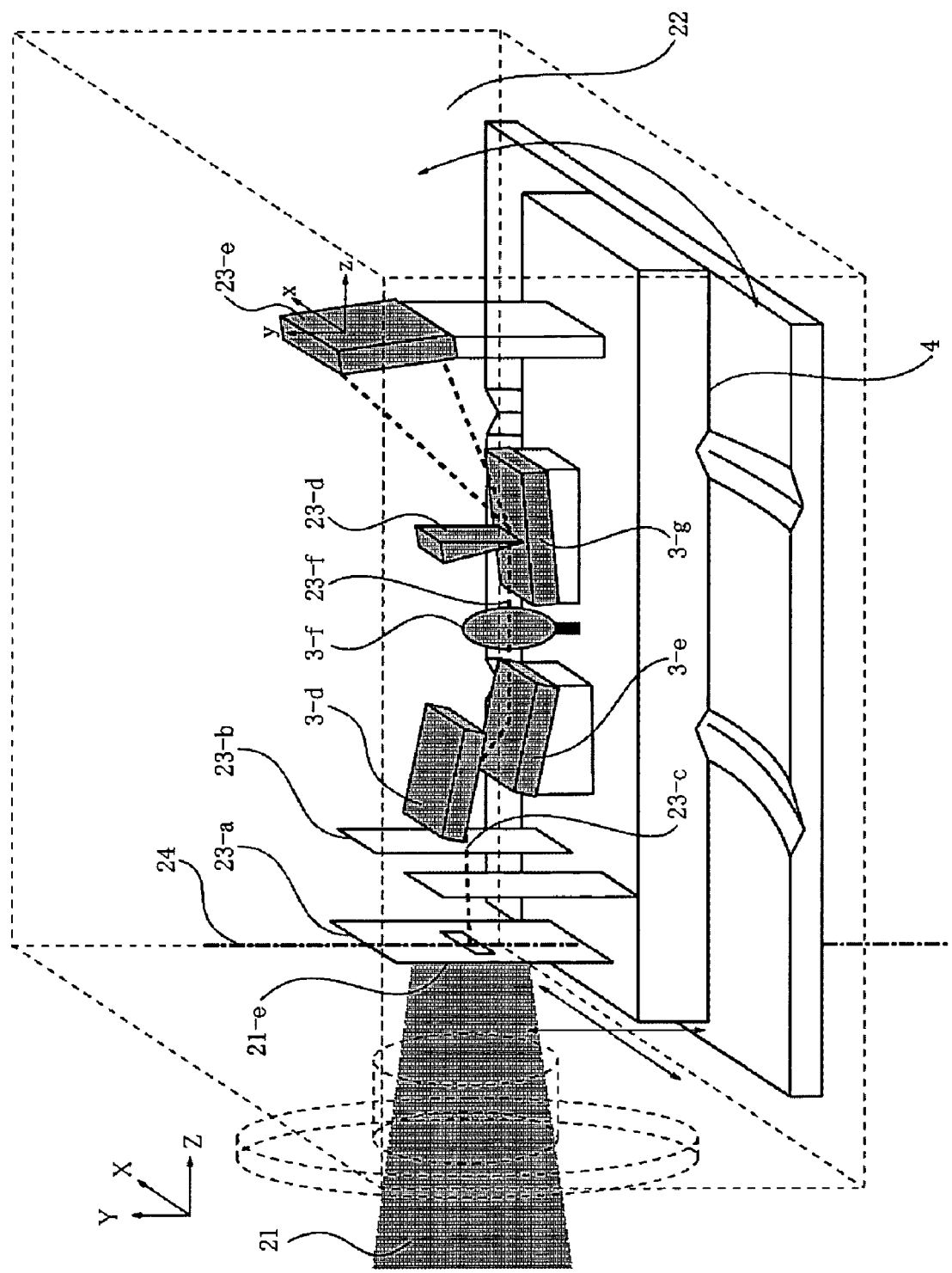
FIG. 4 is a sectional view of an EUV light spectrum measuring apparatus according to a second embodiment.

FIG. 4 is a perspective view of the EUV light spectrum measuring apparatus according to a second embodiment. The following description uses a coordinate axis that defines an Z axis as an optical axis of the EUV light 2 incident upon the EUV light spectrum measuring apparatus 22, a Y axis as a direction perpendicular to a surface that includes the Z axis on which the ωY stage 4 operates, and a X axis as a direction perpendicular to the Y axis and Z axis.

For the inside of the EUV light spectrum measuring apparatus 22 in FIG. 4, a description will be given with a local coordinate (x, y, z) which is different from the whole coordinate (X, Y, Z), and defines a Z axis as an optical-axis direction at each position in the optical path, an x axis as a direction perpendicular to the z axis and Y axis, and y axis as a direction perpendicular to the z axis and X axis. This coordinate (x, y, z) rotates with a reflection on the decentering reflective surface on the optical path, with a rotation of the ωY stage 4 around the Y axis, etc. The plane imaging diffraction grating 3-*g*, which will be described later, is arranged so that its diffracting surface is parallel to the x axis. Those elements in FIG. 4, which are the same as corresponding elements in the EUV light spectrum measuring apparatus the first embodiment, are designated by the same reference numerals in FIG. 1, and a detailed description thereof will be omitted.

In FIG. 4, the EUV light 21 from an EUV light source (not shown) is condensed at a condensing point 21-*e* having a finite size similar to the condensing point 1-*e* in a first embodiment, and enters the EUV light spectrum measuring apparatus 22 around the condensing point 21-*e* as a divergent center point.

A light source position restricting aperture 23-*a* and an x-axis angle restricting aperture 23-*b* are arranged apart from each other by a predetermined distance, and converts EUV light on a specific position on the condensing point 21-*e* having the finite size into EUV light 23-*c* having an approximately constant directivity. While FIG. 4 arranges the light source position restricting aperture 23-*a* at the condensing point 21-*e*, the preferred embodiment is not limited to this arrangement.

If necessary, reflections on the high order light cutting mirrors 3-*d* and 3-*e* remove a wavelength component corresponding to the high order light from the EUV light 23-*c*, and the visible light cutting filter 3-*f* cuts the unnecessary visible right and infrared light.

The EUV light 23-*c* enters the plane imaging diffraction grating 3-*g* for spectrum splitting around the x axis, and then enters a CCD 23-*e* as a detector. A Y-axis angle restricting edge aperture 23-*d* provided in an approximately perpendicular to the plane imaging diffraction grating 3-*g* enables only the EUV light that is restricted to a specific direction on the YZ plane to enter the CCD 23-*e*, improving the resolution of the split spectrum. In FIG. 4, when the light enters the CCD 23-*e* as a detector, the light having a short wavelength is dispersed in the minus side of the y axis and the light having a long wavelength is dispersed in the plus side of the y axis.

In order to improve the spectrum resolution detected by the EUV light spectrum measuring apparatus 22 shown in FIG. 4, the narrow width of the incident light upon the plane imaging diffraction grating 3-*g* in the y axis direction is preferable. Unless this condition is met, the lights diffracted at different positions on the plane imaging diffraction grating 3-*g* superimpose on the CCD 23-*e* and the original spectrum is unavailable. On the other hand, use of the plane imaging diffraction grating 3-*g* apart from the condensing point 21-*e* by a predetermined distance, a light source image is formed on the CCD 23-*e* arranged apart by a predetermined distance and the light included in the incident light does not have to be made collimated light.

In order to narrow a width in the y axis direction of the incident light upon the plane imaging diffraction grating 3-*g*, it is effective to provide a Y-axis angle restricting edge aperture 23-*d* and to restrict an optical path width (in the y-axis direction) which is diffracted on the plane imaging diffraction grating 3-*g* and introduced to the CCD 23-*e*. When the Y-axis angle restricting edge aperture 23-*d* is provided just near the plane imaging diffraction grating 3-*g*, only the light diffracted below the Y-axis angle restricting edge aperture 23-*d* reaches the CCD 23-*e*.

On the other hand, the spread in the x-axis direction of the incident light upon the plane imaging diffraction grating 3-*g* does not affect the measurement precision of the spectrum. In the structure shown in FIG. 4, the EUV lights incident upon different positions on the x axis on the CCD 23-*e* are the EUV lights having different divergent directions on the ZX plane. Therefore, one measurement can measure the spectrum in the wide range on the ZX plane by elongating a length in the x-axis direction of the measurement system that includes the plane imaging diffraction grating 3-*g* and the CCD 23-*e*, and by elongating a width in the x-axis direction of the passing light restricted by the x-axis angle restricting aperture 23-*b* etc.

In order to widen the measurable range in the divergent direction by one measure, a distance from the condensing point 21-*e* to the plane imaging diffraction grating 3-*g* should be shortened.

As discussed, as a section of the measured light that is shaped by the apertures 23*a*, 23*b*, and 23*d* is made narrow in the y-axis direction orthogonal to the plane imaging diffraction grating 3-*g*, and made wide in the x-axis direction orthogonal to the y-axis direction, the spectrum of the EUV light which disperses in a wide range can be measured at one time and the measurement accuracy of the spectrum can be improved. In particular, the resolution in each dispersion direction can be made constant when the apertures 23*a*, 23*b* and 23*d* finally shape a section of the measured light in a rectangle that is long in the x-axis direction.

In order to implement the above embodiment, the following concrete structure is preferable: In an opening of the light source position restricting aperture 23-*a*, a width in the x-axis direction is longer than the width in the Y-axis direction but sufficiently smaller than a width in the x-axis direction in an opening of the x-axis angle restricting aperture 23-*b* as shown in FIG. 4. A size and direction of the x-axis angle restricting aperture 23-*b* approximately controls the restriction in the divergent direction of the EUV light on the ZX plane. It is preferable to make the width in the x-axis direction in the opening of the x-axis angle restricting aperture 23-*b* greater than the widths in the Y-axis direction in the opening of the plane imaging diffraction grating 3-*g* and the Y-axis angle restricting edge aperture 23-*d*, and to make a distance between the condensing point 21-*e* and the x-axis angle restricting aperture 23-*b* smaller than a distance between the condensing point 21-*e* and the Y-axis angle restricting edge aperture 23-*d*.

Thereby, the EUV light capture angle allowed by the light source position restricting aperture 23-*a* and x-axis angle restricting aperture 23-*b* on the ZX plane is greater than the EUV light capture angle allowed by the light source position restricting aperture 23-*a* and Y-axis angle restricting aperture 23-*d* on the YZ plane.

Thus, a section of the measured light 23-*f* incident upon the plane imaging diffraction grating 3-*g* has a shape that has different widths in two orthogonal directions, making the width in the y-axis direction greater than that in the x-axis direction. In addition, it is preferable that the size of the x-axis angle restricting aperture 23-*b* is set so that the width in the x-axis direction of the measured light 23-*f* is approximately equal to or greater than the width in the x-axis direction of the CCD 23-*e*.

The above structure can maintain the resolution of the spectrum measurement and enable one measurement to measure the EUV light in different divergent directions on the ZX plane.

The spectra of the lights in all the directions that diverge from the condensing point 21-*e* on the ZX plane can be measured by fixing the spectrum measuring means 21-*e* onto the ωY stage 4 that is rotatable around the Y axis around the condensing point 21-*e*, and rotating it as a whole in an arbitrary direction within the ZX plane around the condensing point 21-*e* during measurements. Even in this case, a measurement length that is long in the x-axis direction can make a rotating pitch of the ωY stage 4 rough and shorten the measurement time period.

The light source position restricting aperture 23-*a*, the x-axis angle restricting aperture 23-*b*, the high order light cutting mirror 3-*d* and 3-*e*, the visible light cutting filter 3-*f*, the plane imaging diffraction grating 3-*g*, the Y-axis angle restricting edge aperture 23-*d*, and the CCD 23-*e* in the spectrum measuring means are located on a X stage (not shown) and a Y stage (not shown) together with the ωY stage 4 similar to the first embodiment. These X stage and Y stage and the actuator as an intensity source enable the above elements to translate as a whole on a plane perpendicular to the Z axis as the optical axis of the EUV light source. Therefore, the spectrum of the EUV light that diverges from an arbitrary divergent point on the condensing point 21-*e* can be measured.

The condenser mirror in the EUV light source has a symmetrical shape with respect to the optical axis, and the spectrum distribution for each spectral divergent direction of the EUV light source is often symmetrical with respect to the optical axis. In measuring the EUV light source, as shown in FIG. 4, a rotating mechanism around the X axis is unnecessary, as long as plural elements in the spectrum measuring means are rotated as a whole, for example, only around the Y axis, and the spectra of the lights that diverge from the condensing point 21-*e* in all the directions on the ZX plane can be measured. As a result, the reduced degree of freedom of driving and the driving mechanism or a simple driving structure can advantageously make the second embodiment smaller than the first embodiment.

While this embodiment makes the width in the x-axis direction of the section of the measured light near the CCD 23-*e* equal to or greater than the width of the CCD 23-*e*, the CCD 23-*e* may have a width sufficiently greater than the width in the x-axis direction of the section of the measured light and greater than the angular range of the measured light. In this case, since it is unnecessary to change the CCD arrangement, the spectrum measuring means that is rotated as a whole by the ωY stage 4 includes only the light source position restricting aperture 23-*a*, the x-axis angle restricting aperture 23-*b*, the high order light cutting mirror 3-*d* and 3-*e*, the visible light cutting filter 3-*f*, the plane imaging diffraction grating 3-*g*, and the Y-axis angle restricting edge aperture 23-*d*.

Similar to the first embodiment, the EUV light spectrum measuring apparatus 22 has a vacuum chamber as indicated by a broken line in FIG. 4, the EUV light spectrum measuring apparatus 22 is connected to the EUV light source (not shown) via the vacuum bellows, the EUV light's position along the optical axis does not change the EUV light source even when the air pressure fluctuates in the EUV light source or the EUV light spectrum measuring apparatus 22, and there is a measure to the stray light.

Third Embodiment

A third embodiment will be described which uses the EUV light spectrum measuring apparatus of the first or second embodiment to calculate the intensity in the predetermined wave range among the EUV lights emitted from the divergent center point of the EUV light source.

A description will now be given of the EUV light spectrum measuring apparatus according to the first embodiment. The EUV light spectrum measuring apparatus according to the first embodiment can measure the EUV light spectra in all the divergent directions emitted from a specific position on the divergent center point restricted by the light source position restricting aperture 3-*a*. The spectra of the EUV lights in all the divergent directions at all the positions on the divergent center point can be obtained by repeating the measurement and by moving the light source position restricting aperture 3-*a* with other elements in the spectrum measuring means as a whole in the X-axis and Y-axis directions. The spectra of the EUV light emitted in the divergent direction from the entire divergent center point can be obtained by superimposing the spectrum measurement results in the same divergent direction from all the different positions on the divergent center point. The intensity's absolute value for each wavelength of the EUV light emitted in a predetermined divergent direction from the entire divergent center point can be calculated by adding the intensity's absolute values in a predetermined wave range, if a ratio of an output absolute value of the photodiode array 3-*h* to the intensity's absolute value of the incident EUV light, or an absolute sensitivity, are obtained in advance. The intensity in a predetermined wave range of the EUV light that is emitted in the predetermined divergent direction from the entire divergent center by adding intensity absolute values within a predetermined wave range. The intensity in the predetermined wave range emitted from the entire divergent center point can be calculated by adding the intensity in the predetermined wave range for each divergent direction with respect to all the divergent directions.

When the EUV light spectrum measuring apparatus of the second embodiment is used, the spectra of the EUV light in all the divergent directions from all the positions on the divergent center point can be calculated on the assumption that the EUV light source has a symmetrical characteristic with respect to the optical axis. Similar to the EUV light spectrum measuring apparatus of the first embodiment, the intensity in the predetermined wave range emitted from the entire divergent center point can be calculated. In other words, when the EUV light source has a symmetrical characteristic with respect to the optical axis, the EUV light spectrum measuring apparatus of the second embodiment can measure the spectrum of the EUV light equivalent to the EUV light emitted in an arbitrary direction from an arbitrary position on the divergent center point.

Figure 5:
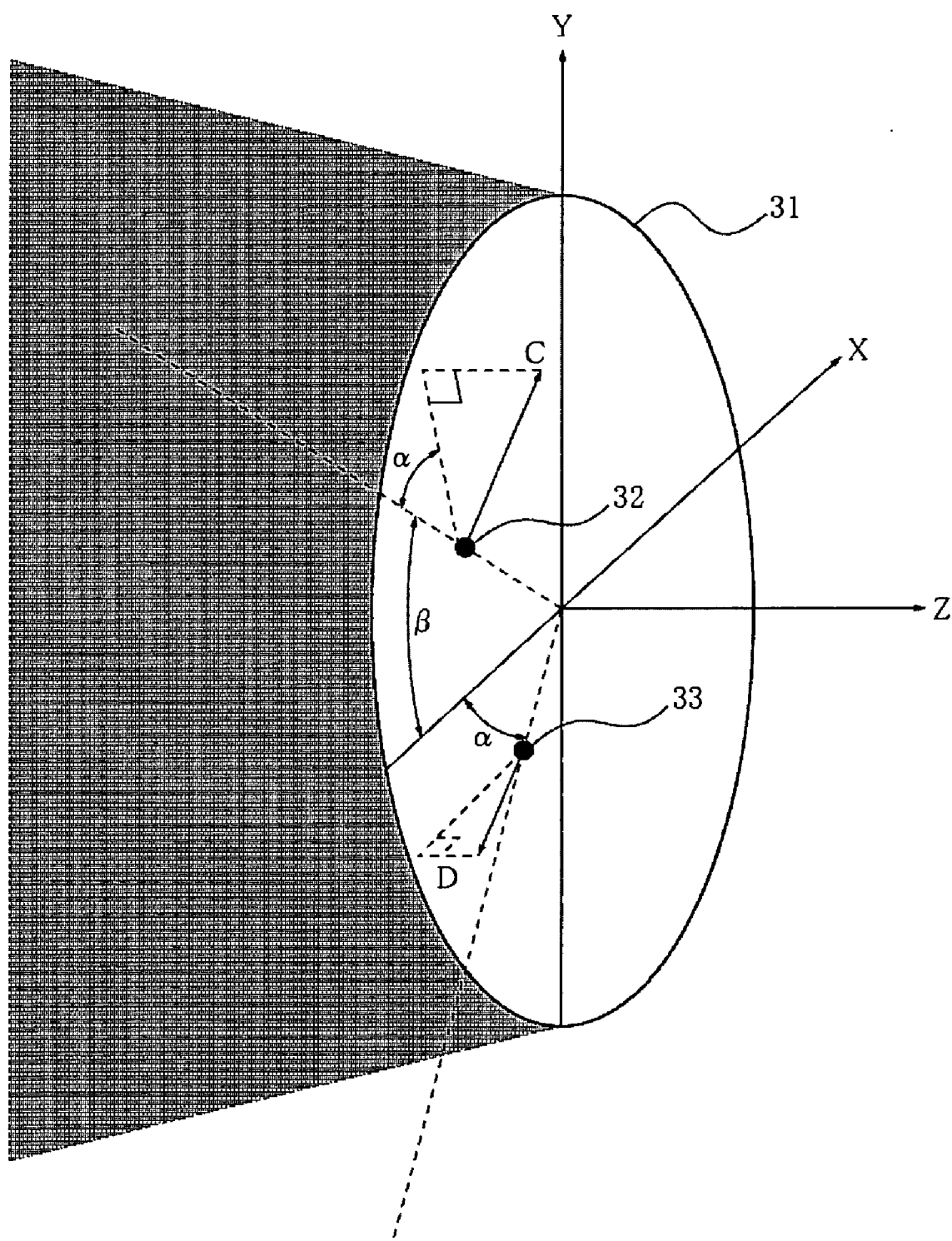
FIG. 5 is a view of the EUV light measurable by the EUV light spectrum measuring apparatus according to the second embodiment, which is equivalent to the EUV light emitted in an arbitrary direction from an arbitrary position on a divergent center point.

FIG. 5 is a view showing the EUV light that is measurable by the EUV light spectrum measuring apparatus of the second embodiment, and is equivalent to the EUV light emitted in an arbitrary direction from an arbitrary position on the divergent center position. In FIG. 5, 31 denotes a condensing point, and it is now attempted to obtain the spectrum of the EUV light emitted from a divergent point 32 at an arbitrary position on a condensing point in an arrow C direction as an arbitrary direction. Since the arrow C direction is not parallel to the ZX plane, the EUV light spectrum measuring apparatus cannot measure directly the spectrum.

However, if a divergent point 33 and an arrow D, which correspond to the divergent point 32 and the arrow C that are rotated by an angle of α+β around the Z axis, have characteristics of a spectrum distribution of the EUV light source, etc. are symmetrical with respect to the optical axis, the equivalency of the spectrum of the EUV light emitted in the arrow C direction from the divergent position 32 is maintained. Here, since the arrow D is parallel to the ZX plane, the EUV light spectrum measuring apparatus of the second embodiment can measure the spectrum of the EUV light emitted in the arrow D direction from the divergent position 33. Therefore, the spectrum of the EUV light emitted in the arrow C direction from the divergent by measuring the spectrum of the EUV light emitted in the arrow D direction from the divergent position 33.

Similarly, the EUV light spectrum measuring apparatus of the second embodiment can calculate the spectra of the EUV lights in all the divergent directions on all the divergent center points. Therefore, when the absolute sensitivity of the CCD 23-*e* is previously calculated, the intensity in the predetermined wave range emitted from the entire divergent center can be independently calculated, similar to the EUV light spectrum measuring apparatus of the first embodiment.

The above embodiment thus calculates the intensity in the predetermined wave range by previously and independently calculating the absolute sensitivity of the photodiode array 3-*h* and CCD 23-*e* to the incident intensity. On the other hand, if, as a result of measurements using another sensor having a known sensitivity to wavelengths including a desired predetermined wave range, the absolute value of the intensity in the wave range that covers this sensor's sensitivity is known for each divergent direction from the entire divergent center point, the previous acquirements of the absolute sensitivity of the photodiode array 3-*h* and the CCD 23-*e* are unnecessary. Since the measurements using the EUV light spectrum measuring apparatus of the first and second embodiments clarify the intensity ratio for each wavelength of the EUV light emitted from the entire divergent center point, and thereby a ratio of the intensity in the desired predetermined wave range is calculated among the intensity for each divergent direction based on the measurements of the above sensor, the intensity in the predetermined wave range emitted from the entire divergent center point can be calculated.

The present invention thus can precisely measure an angular distribution of the EUV light spectrum that diverges arbitrary directions from the condensing point in the EUV light source. The intensity of the EUV light can be precisely calculated by calculating the intensity in a predetermined wave range for each divergent direction based on the spectrum distribution for each divergent direction calculated by measurements using the EUV light spectrum measuring apparatus, and adding the intensity in the predetermined wave range for each divergent direction with respect to all the divergent directions.

This application claims a foreign priority based on Japanese Patent Application No. 2004-044724, filed Feb. 20, 2004, which is hereby incorporated by reference herein.

What is claimed is:

1. A measuring apparatus for measuring a spectrum of extreme ultraviolet light that diverges from a divergent center point of an extreme ultraviolet light source, said measuring apparatus comprising: a spectrum measuring unit that includes a spectrometer and a detector that has a spatial resolution in a spectrum forming direction of the spectrometer; and a drive mechanism that makes the spectrum measuring unit movable relative to the divergent center point.

2. A measuring apparatus according to claim 1, wherein a movement by said drive mechanism is a rotation of the spectrum measuring unit on a sphere around a predetermined point.

3. A measuring apparatus according to claim 1, wherein the spectrum measuring unit further includes an aperture for restricting light incident upon the spectrometer, a section of measured light shaped by the aperture having different widths in two orthogonal directions, wherein the spectrometer is arranged so that a spectral direction by the spectrometer is approximately perpendicular to a longitudinal direction of the section of the measured light.

4. A measuring apparatus exposure apparatus according to claim 3, wherein a movement by said drive mechanism is a rotation of said spectrum measuring unit around a predetermined point on a surface parallel to the longitudinal direction of the section of the measured light and an optical axis of an extreme ultraviolet light source.

5. A measuring apparatus exposure apparatus according to claim 1, wherein a movement by said drive mechanism is a translation of said spectrum measuring unit on a surface perpendicular to an optical axis of an extreme ultraviolet light source.

6. A measuring apparatus exposure apparatus according to claim 1, wherein a movement by said drive mechanism is a rotation of said spectrum measuring unit around an optical axis of an extreme ultraviolet light source.

* * * * *